United States Patent [19]

Yoshida et al.

[11] 4,131,743
[45] Dec. 26, 1978

[54] PROCESS FOR PREPARING UNSATURATED DIESTERS

[75] Inventors: Yoshinori Yoshida, Yokohama; Tutomu Kobayashi, Ibaraki; Hironobu Shinohara, Yokohama; Izumi Hanari, Tokyo, all of Japan

[73] Assignee: Japan Synthetic Rubber Co., Ltd., Tokyo, Japan

[21] Appl. No.: 702,935

[22] Filed: Jul. 6, 1976

[30] Foreign Application Priority Data

Jul. 17, 1975 [JP] Japan .................................. 50/86657
Dec. 11, 1975 [JP] Japan .................................. 50/146902

[51] Int. Cl.² ............................................ C07C 67/05
[52] U.S. Cl. ........................................ 560/244; 560/1; 560/112; 252/472
[58] Field of Search ................... 260/497 A; 560/244, 560/1, 112

[56] References Cited

U.S. PATENT DOCUMENTS

| | | | |
|---|---|---|---|
| 3,622,620 | 11/1971 | Horiie .............................. | 260/497 A |
| 3,637,819 | 1/1972 | Sennewald ....................... | 260/497 A |
| 3,872,163 | 3/1975 | Shimiza ........................... | 260/497 A |
| 3,922,300 | 11/1975 | Onoda .............................. | 260/497 A |
| 3,959,352 | 5/1976 | Onoda .............................. | 260/497 A |

Primary Examiner—James O. Thomas, Jr.
Assistant Examiner—Michael Shippen
Attorney, Agent, or Firm—Stevens, Davis, Miller & Mosher

[57] ABSTRACT

Unsaturated diesters are produced by a process which comprises reacting, in a flowing gaseous phase, a gaseous mixture comprising a conjugated diene, a carboxylic acid and molecular oxygen in the presence of (A) a catalyst comprising palladium, vanadium, antimony and at least one alkali metal carboxylate, or in the presence of (B) a catalyst comprising palladium, vandium, antimony, at least one alkali metal carboxylate and at least one alkali metal halide. The catalyst (A) maintains a high activity and a high selectivity for a long time. The catalyst (B), in which further the alkali metal halide is added, shows a higher activity and a higher selectivity for a longer time. And its activity and selectivity are stable and durable at high temperatures such as 160° - 200° C. Furthermore, the addition of the alkali metal halide suppresses combustion reaction of dienes such as butadiene remarkably. Additionally, the catalysts (A) and (B), especially (B) can be easily reactivated when they lose activity.

25 Claims, No Drawings

PROCESS FOR PREPARING UNSATURATED DIESTERS

This invention relates to a process for preparing or producing unsaturated diesters from a conjugated diene, a carboxylic acid and molecular oxygen.

And more particularly, it relates to a process for producing unsaturated diesters which comprises reacting, in a flowing gaseous phase, a gaseous mixture comprising a conjugated diene, a carboxylic acid and molecular oxygen in the presence of (A) a catalyst comprising palladium, vanadium, antimony and at least one alkali metal carboxylate, or in the presence of (B) a catalyst comprising palladium, vanadium, antimony, at least one alkali metal carboxylate and at least one alkali metal halide.

Heretofore, there have been proposed various processes for preparing esters from olefins or dienes by reacting with carboxylic acids and oxygen in the presence of a catalyst comprising palladium as the main component.

For instance, various processes for preparing butenediol diesters from butadiene in the presence of a catalyst comprising palladium have been researched and disclosed in many literature.

However, the catalysts in the conventional processes are not always satisfactory in respects of the activity, selectivity, stability and durability.

It has been proposed that unsaturated glycol diesters are prepared by reacting, in a gaseous phase, a conjugated diene, a carboxylic acid and molecular oxygen in the presence of a catalyst comprising palladium, antimony and at least one alkali metal carboxylate (e.g. Japanese Patent Application KOKAI No. 4416/1973).

In the aforementioned process, however, the catalysts have various disadvantages in respects of activity, selectivity, stability and durability.

As for a catalyst comprising the three components of palladium, vanadium and an alkali metal carboxylate, it has been noted that the catalyst shows extremely low activity, and therefore it is practically impossible to employ the catalyst in a process for producing the products of this invention.

An object of this invention is to provide a commercially useful process for producing an unsaturated diester, especially an unsaturated glycol diester in which acyl-oxy groups have been added to the both side ends of the conjugated diene compound.

Other objects and advantages of this invention will be apparent from the following descriptions.

We made research on processes for producing unsaturated diesters by reacting a conjugated diene, a carboxylic acid and molecular oxygen in a flowing gaseous phase, and we found that a catalyst comprising palladium, vanadium, antimony and at least one alkali metal carboxylate maintains a high activity and a high selectivity for a long time.

The catalyst comprising the four components, that is, palladium, vanadium, antimony and at least one alkali metal carboxylate, eliminates the above mentioned disadvantages of the conventional processes.

Further, we found that a catalyst, in which at least one alkali metal halide is added further in addition to the above mentioned four components, shows remarkably a higher activity and a higher selectivity for a longer time. Its high activity and high selectivity are stable and durable at high temperatures such as 160–200° C.

Furthermore, the addition of the alkali metal halide suppresses combustion reaction of dienes such as butadiene remarkably and also prevents by-production of monobutadienylacetate especially when lowering $O_2$/diene ratio in a feed gaseous mixture.

The compounds, alkali metal carboxylates and alkali metal halides, respectively act as activity-promoting components.

The inventors of this invention found also that a catalyst which has been used and lost its activity can be reactivated by means of a method which comprises washing out the alkali metal carboxylate and alkali metal halide when it is used, which acted as activity-promoting component(s), with a liquid comprising water and/or alcohol, thereafter sintering at 150–500° C. with a gas containing oxygen and then reducing at 100–500° C. with a reducing gas, and finally readding the said activity-promoting component(s). The resulting reactivated catalyst shows surprisingly the same high activity, the same high selectivity and the same good stability and durability as the original catalyst.

Furthermore, we found an alternative method for reactivating a catalyst which comprises treating the catalyst which has been used and whose activity has been lowered in our above mentioned processes for producing unsaturated diesters with a gas containing steam at 100–600° C.

According to said method, when the catalyst is treated in a stage of still retaining more than 50% of the original activity, the treated catalyst recovers the same activity as the original catalyst.

Conjugated dienes represented by the following formula may be used in this invention.

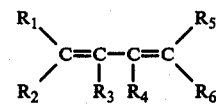

Wherein $R_1$ - $R_6$ individually are hydrogen or hydrocarbon groups, preferably alkyl groups. The number of carbon atoms of hydrocarbon groups is not limited, but preferably 1 to 6.

The above conjugated dienes include butadiene, isoprene, 2,3-dimethyl butadiene, piperylene and the like.

Cyclic conjugated dienes such as cyclopentadiene, alkyl-cyclopentadiene, cyclohexadiene and the like also may be used in this invention.

Among such conjugated dienes, butadiene and isoprene are especially preferable.

It is not necessary for said conjugated dienes to be pure and they may include other hydrocarbons in a ratio not affecting the reaction.

Carboxylic acids which may be used in this invention include aliphatic, alicyclic and aromatic carboxylic acids. For commercial application, lower aliphatic carboxylic acids such as acetic acid, propionic acid, butyric acid and the like are preferable.

Oxygen acting as an oxidizing agent is not required to be pure. It may be diluted by at least one inert gas such as nitrogen, carbon dioxide and the like. Air is the most convenient oxygen source, since it is available anywhere, and not expensive.

When acetic acid and butadiene are employed as the starting materials, the main reaction proceeds as follows:

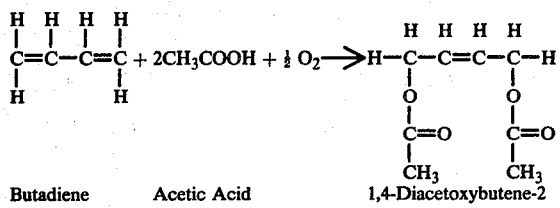

Butadiene   Acetic Acid   1,4-Diacetoxybutene-2

According to this invention, 1,4-diacetoxybutene-2 is produced with a high selectivity, and only a small ratio of 3,4-diacetoxybutene-1 and monoacetoxy-1,3-butadiene are produced as by-products.

Preparing procedures for our catalysts can be carried out by the conventional methods. For example, the metal compounds of the catalyst are dissolved in a solvent. Into the resulting solution, a carrier is dipped. Thereafter the said components are fixed on the carrier by distilling off the solvent and reduced by hydrogen or an organic reducing agent in a gaseous phase or by the conventional reducing agents such as hydrazine, formaldehyde and the like. Thereafter, alkali metal carboxylates and when used also alkali metal halide acting as an activity-promoting component or activity promoter, are fixed on the carrier.

Said preparation method of catalysts is only one of the methods which may be used in this invention and its variations may be adopted. For example, vanadium as one of the metal components of the catalyst is fixed on a carrier at first and then the other components are fixed thereon.

Alternatively, at least one alkali metal carboxylate, or in addition thereto at least one alkali metal halide may be added to the reaction system.

In the first reactivating method of the catalysts before mentioned, the activity promoter which was washed out at the first stage can be utilized as the activity promoter to be added at the final stage of the method.

Carriers which may be used in this invention include alumina, silica-alumina, silica, active carbon, magnesia, diatomaceous earth, carborundum and the like. Especially, alumina and silica-alumina are preferable.

Palladium compounds which may be used in this invention include palladium halides such as palladium chloride, etc., organic salts of palladium such as palladium acetate, etc., palladium nitrate, palladium oxide, palladium sulphate and the like.

Amounts of palladium in the catalysts can be varied in a wide range, but amounts from 0.1 to 10% by weight based on the carrier are preferable.

Vanadium compounds include vanadium halides such as vanadium chloride, vanadium bromide, etc., vanadium oxyhalide such as vanadyl chloride, vanadyl bromide, etc., ammonium metavanadate, vanadyl sulfide, vanadium oxide and the likes. Especially ammonium metavanadate is preferable.

Antimony compounds include antimony halides such as antimony chloride, antimony bromide, etc., organic salts of antimony such as antimony acetate, etc., antimony oxide, antimony sulfide, metal antimony and the like.

Amounts of vanadium and antimony in the catalysts are preferably in the range of from 0.01 to 20 gram atoms, more preferably from 0.1 to 10 gram atoms per 1 gram atom of palladium.

Ratio of antimony/vanadium is not limited but is preferably in the range of from 0.1 to 10 in terms of gram atoms.

Alkali metal carboxylates include lithium-, sodium-, potassium-, rubidium-, or caesium-carboxylate and the like.

Alkali metal carboxylates can be fixed on the carrier in the ratio of 0.01–40 m mol per 1 g of carrier.

Alkali metal halides include fluorides, chlorides, bromides and iodides of lithium, sodium, potassium, rubidium and caesium such as lithium fluoride, sodium fluoride, potassium fluoride, rubidium fluoride, caesium fluoride, lithium chloride, sodium chloride, potassium chloride, rubidium chloride, caesium chloride, lithium bromide, sodium bromide, potassium bromide, rubidium bromide, caesium bromide, lithium iodide, sodium iodide, potassium iodide, rubidium iodide and caesium iodide.

Among these alkali metal halides, alkali metal chlorides, especially caesium chloride, are preferable.

Alkali metal halides can be fixed on the carrier in the ratio of 0.01–40 m mol per 1 g of carrier.

As for the methods for carrying out the reaction in commercial applications, a fixed bed method, a fluidized method or the like can be adopted case by case.

The reaction temperatures and the reaction pressures can be selected from the range which is used in the conventional processes and will not be restricted. Usually, the reaction is carried out at temperatures of 100–300° C., preferably 100–200° C. and under such pressures that the starting reactants and the products can remain in a gaseous state.

Each content of a conjugated diene, a carboxylic acid and oxygen in a gaseous mixture is not limited and can be varied in the range of 1 to 98 percent by volume based on the mixture thereof.

Preferably, the content of a conjugated diene can be varied from 1 to 85 percent by volume, the content of a carboxylic acid can be varied from 5 to 85 percent by volume and the content of oxygen can be varied from 1 to 50 molar percent, based on the mixture thereof. But, care should be taken so that the composition of the gases may not be in the range of an explosive condition. Inert gases such as nitrogen, steam and the like may be added as diluting material in this invention.

Examples and comparative examples, in which the determination of products is carried out by means of gas chromatography, are as follows.

EXAMPLE 1

0.334 g of palladium chloride anhydrate, 0.220 g of ammonium metavanadate and 0.428 g of antimony trichloride were dissolved in 20 ml of 10% hydrogen chloride aqueous solution to prepare a solution. 20 g of carrier (globular silica-alumina, 4–6 mm φ, silica content 10%) was previously sintered for 3 hours at 1200° C. and dipped into the above mentioned solution. The carrier taken out of the solution was dried in a nitrogen stream for two hours at 150° C. and reduced by hydrogen gas which was fed at a flow rate of 100 ml/min. for five hours at 400° C. The content of palladium was about 1.0% by weight based on the carrier.

The resulting treated carrier was dipped for one night in 15 ml of solution in which 2.0 g of potassium acetate was dissolved and then dried at 80° C. for two hours under the reduced pressure of 50 mm Hg.

10 ml of the prepared catalyst was packed in a flowing reaction tube made of Pirex, having a 20 mm inner diameter. A gaseous mixture comprising butadiene, acetic acid and air (20:20:60, volume ratio) was introduced into the said reactor at a flow rate of 10 l/hr and reacted at a temperature of 140° C. The result is shown in Table 1.

COMPARATIVE EXAMPLE 1

A catalyst was prepared without ammonium metavanadate and the other procedures of the catalyst preparation and the reaction was carried out under the same conditions as in Example 1. The result is shown in Table 1.

COMPARATIVE EXAMPLE 2

A catalyst was prepared without antimony trichloride and the other procedures of the catalyst preparation and the reaction were carried out under the same conditions as in Example 1. The result is shown in Table 1.

EXAMPLES 2–6

Catalysts were prepared so that the fixed content of metal palladium was 1.0% by weight based on the carrier. The contents of metal vanadium and metal antimony were varied in terms of gram atom ratio.

The other procedures were carried out under the same conditions as in Example 1. The results are shown in Table 2.

EXAMPLE 7

A catalyst was prepared by the same method as in Example 1. A gaseous mixture comprising isoprene, acetic acid and air (5:20:75, volume ratio) was fed to the reactor at a flow rate of 5 l/hr and reacted at 160° C. in a flowing gas phase. The products sampled at 25 hours after starting were determined. The result showed that 65.1 g/l of cat. hr of 1,4-diacetoxy-2-methyl-butene-2, 6.0 g/l of cat. hr of the sum of 3,4-diacetoxy-3-methyl-butene-1 and 3,4-diacetoxy-2-methyl-butene-1, and 5.2 g/l of cat. hr of isoprenyl-monoacetate were produced.

EXAMPLE 8

A catalyst was prepared by the same method as in Example 1 except replacing 2.5 g of potassium propionate in place of 2.0 g of potassium acetate in Example 1.

A gaseous mixture comprising butadiene, propionic acid and air (20:30:50, volume ratio) was fed to the reactor at a flow rate of 7.5 l/hr and reacted at 150° C. The result showed that 95.3 g/l of cat. hr of 1,4-dipropionoyloxy-butene-2, 4.6 g/l of cat. hr of 3,4-dipropionoyloxy-butene-1 and 7.2 g/l of cat. hr of butadienyl-monopropionate were prepared.

EXAMPLE 9

0.334 g of palladium chloride anhydrate, 0.220 g of ammonium metavanadate and 0.428 g of antimony trichloride were dissolved in 20 ml of 10% hydrogen chloride aqueous solution.

20 g of carrier (globular silica-alumina, 4–6 mm $\phi$, including 10% of silica) was previously sintered for 3 hours at 1200° C. and dipped into said solution. The carrier was dried in a nitrogen stream for two hours at 150° C. and then reduced by hydrogen gas which was fed at a flow rate of 100 ml/min. for five hours at 400° C.

The resulting treated carrier was dipped for one night in 30 ml of an aqueous solution in which 3.367 g of caesium chloride and 3.839 g of caesium acetate were dissolved and then dried at 80° C. for two hours under the reduced pressure of 50 mm Hg.

10 ml of the catalyst was packed in a flowing reaction tube made of Pirex having 20 mm of the inner diameter. A gaseous mixture comprising butadiene, acetic acid, nitrogen and oxygen (5:20:60:15, volume ratio) was fed to the said reactor at a flow rate of 10 l/hr and reacted at 140° C. The result is shown in Table 3.

COMPARATIVE EXAMPLE 3

A catalyst was prepared without caesium chloride and the other procedures of the catalyst preparation and the reaction were carried out under the same conditions as in Example 9. The result is shown in Table 3.

COMPARATIVE EXAMPLE 4

A catalyst was prepared without caesium chloride but using 7.678 g of caesium acetate instead of 3.839 g and the other procedures of the catalyst preparation and the reaction were carried out under the same conditions as in Example 9. In this case, the amount of caesium in this Comparative Example was the same as in Example 9. The result is shown in Table 3.

COMPARATIVE EXAMPLE 5

A catalyst was prepared without caesium acetate and the other procedures of the catalyst preparation and the reaction were carried out under the same conditions as in Example 9. The result is shown in Table 3.

COMPARATIVE EXAMPLE 6

A catalyst was prepared without caesium acetate but using 6.734 g of caesium chloride instead of 3.367 g and the other procedures of the catalyst preparation and the reaction were carried out under the same conditions as in Example 9. The amount of caesium in this Comparative Example was the same as in Example 9. The result is shown in Table 3.

EXAMPLE 10

A catalyst was prepared by means of the same method as in Example 9 except substituting 2.0 g of potassium acetate for 3.839 g of caesium acetate. The other conditions were the same as in Example 9. The result is shown in Table 4.

EXAMPLE 11

A catalyst was prepared by means of the same method as in Example 9 exceot substituting 1.0 g of potassium acetate for 3.839 g of caesium acetate. A gaseous mixture comprising, butadiene, acetic acid, nitrogen and oxygen (20:20:48:12, volume ratio) was fed to the reactor at a flow rate of 10 l/hr and reacted at 140° C. The result is shown in Table 4.

EXAMPLE 12

A catalyst was prepared by means of the same method as in Example 9 except substituting 4.0 g of potassium acetate for 3.839 g of caesium acetate and 1.683 g of caesium chloride for 3.367 g.

The other procedures were carried out under the same conditions as in Example 11. The result is shown in Table 4.

EXAMPLES 13–18

Catalysts were prepared by means of the same method as in Example 9 except substituting potassium acetate for caesium acetate and alkali metal halides shown in Table 5 for caesium chloride. The other procedures were carried out under the same conditions as in Example 11. The results are shown in Table 5.

EXAMPLE 19

A catalyst was prepared and packed by means of the same method as in Example 9. A gaseous mixture comprising isoprene, acetic acid, nitrogen and oxygen (20:20:48:12, volume ratio) was fed to the reactor at a flow rate of 5 l/hr and reacted at 150° C. in a flowing gas phase.

The products sampled at fifty hours after starting were analyzed and determined. The results showed that 71.5 g/l of cat. hr of 1,4-diacetoxy-2-methyl-butene-2 was produced with a high selectivity of 91.2%.

EXAMPLE 20

1.17 g of palladium chloride anhydrate, 2.14 g of antimony trichloride and 1.10 g of ammonium metavanadate were dissolved in 100 ml of 10% hydrogen chloride aqueous solution.

100 g of carrier (globular silica-alumina, 4–6 mm $\phi$ including 10% of silica) was previously sintered for 3 hours at 1200° C. and dipped into the said solution.

The carrier was dried in a nitrogen stream for two hours at 150° C. and then reduced by hydrogen gas which was fed at a flow rate of 100 ml/min for 5 hours at 400° C.

The carrier was dipped for one night in 100 ml of aqueous solution in which 34.4 g of caesium chloride and 10.0 g of potassium acetate were dissolved and then dried at 80° C. for two hours under the reduced pressure of 50 mm Hg.

100 ml of the catalyst was packed in a flowing reaction tube made of stainless steel having 38 mm of the inner diameter. A gaseous mixture comprising butadiene, acetic acid, nitrogen and oxygen (20:20:48:12, volume ratio) was fed into the said reactor at a flow rate of 100 l/hr and reacted at 140° C. The result is shown in Table 6.

EXAMPLE 21

A catalyst was prepared under the same conditions as in Example 20 and the reaction was carried out at 180° C.

1.8–2.0% by weight of the feed butadiene was burned and converted to $CO_2$ at any time during reaction. The result is shown in Table 6.

EXAMPLE 22

A catalyst was prepared under the same conditions as in Example 20. A gaseous mixture comprising butadiene, acetic acid, nitrogen and oxygen (20:20:5:55, volume ratio) was fed into the reactor at a flow rate of 50 l/hr and reacted at 180° C. Less than 1% by weight of the feed butadiene was converted to $CO_2$ at any time during reaction. The result is shown in Table 6.

COMPARATIVE EXAMPLE 7

A catalyst was prepared without caesium chloride and the other procedures of the catalyst preparation and the reaction were carried out under the same conditions as in Example 21. The reaction proceeded out of order from the beginning of the reaction, especially it was very difficult to control the reaction temperature.

COMPARATIVE EXAMPLE 8

A catalyst was prepared without caesium chloride and the other procedures of the catalyst preparation and the reaction were carried out under the same conditions as in Example 22. The reaction proceeded out of order from the beginning of the reaction, especially it was very difficult to control the reaction temperature.

COMPARATIVE EXAMPLE 9

The procedures of the catalyst preparation and the reaction were carried out under the same conditions as in Comparative Example 8 except that the reaction temperature was 140° C. instead of 180° C.

2.5–3.0% by weight of the feed butadiene was burned and converted to $CO_2$ which was higher than in Example 21.

EXAMPLE 23

3.34 g of palladium chloride, 2.20 g of ammonium metavanadate and 4.28 g of antimony trichloride were dissolved in 200 ml of 10% hydrogen chloride aqueous solution to prepare a solution. 200 g of carrier (globular silica-alumina, 4–6 mm $\phi$, silica content 10%) was previously sintered for 3 hours at 1200° C. and dipped in the above mentioned solution. The carrier taken out of the solution was dried in a nitrogen stream at 200° C. for 2 hours and reduced at 400° C. for 4 hours by flowing hydrogen gas at a flow rate of 100 ml/min.

The resulting catalyst contains palladium at the ratio of 1.0% by weight on the basis of carrier and the ratio of Pd, V, and Sb in terms of gram atom is 1:1:1.

The resulting treated carrier was dipped for one night in an aqueous solution of 200 ml in which 68.8 g of caesium chloride and 20.0 g of potassium acetate were dissolved. Thereafter the carrier was taken out of the solution and dried for 2 hours under the reduced pressure of 50 mm Hg.

100 ml of the catalyst was packed in a flowing reaction tube made of stainless steel having an inner diameter of 38 mm.

A gaseous mixture containing butadiene, acetic acid, nitrogen and oxygen (20:20:48:12 volume ratio) was fed into the reactor at a flow rate of 100 l/hr and reacted at 140° C.

As the results, diacetoxybutene was produced at the yield of 163.4 g/l cat. hr and with the selectivity of 98.3% at the stage of 100 hours after starting and at the yield of 55.0 g/l cat. hr with the selectivity of 94.2% at the stage of 600 hours after starting. Because the yield decreased, the reaction was stopped at 600 hours after starting.

The catalyst which lost its activity was washed four times with dipping in water at 90° C. for 2 hours and then dried in a nitrogen stream and sintered for 3 hours at 300° C. by flowing air at the rate of 1 l/min. Thereafter the catalyst was reduced at 200° C. for 5 hours by flowing hydrogen gas at the rate of 100 ml/min. and dipped for one night in an aqueous solution of 100 ml in which 34.4 g of caesium chloride and 10.0 g of potassium acetate were dissolved and finally dried.

The flowing gaseous phase reaction was carried out under the same conditions as mentioned above in the presence of the reactivated catalyst.

As the results, diacetoxybutene was produced at the yield of 167.3 g/l cat. hr with the selectivity of 98.2% at the stage of 100 hours after starting and at the yield of 60.3 g/l cat. hr with the selectivity of 94.1% at the stage of 600 hours after starting. These results show that the catalyst can be reactivated almost completely. Furthermore, the recycling of reactivation-reaction was carried out five times. The results show that the activity decreases by 6.2% at the stage of 100 hours after starting and by 3.5% at the stage of 600 hours after starting, in comparison with the original activity and the selectivity is maintained within plus-minus 1.0% of the original selectivity.

EXAMPLE 24

A catalyst was prepared by means of the same method as in Example 23 except substituting 17.4 g of potassium fluoride for caesium chloride. The reaction was carried out under the same conditions as in Example 23. The result shows that diacetoxybutene was produced at the yield of 143.3 g/l cat.hr with the selectivity of 95.6% at the stage of 100 hours after starting and at the yield of 47.3 g/l cat.hr with the selectivity of 89.2% at the stage of 400 hours after starting.

The reaction was stopped at the stage of 400 hours after starting and the catalyst was reactivated by the same method as in Example 23.

As the results, diacetoxybutene was produced at the yield of 136.2 g/l cat.hr with the selectivity of 96.1% at the stage of 100 hours after starting.

EXAMPLE 25

A catalyst was prepared by means of the same method as in Example 23 and packed in the same reactor as in Example 23.

A gaseous mixture containing butadiene, acetic acid, nitrogen and oxygen (20:20:48:12, volume ratio) was fed into the reactor at a flow rate of 100 l/hr and reacted at 140° C.

As the results, diacetoxybutene was produced at the yield of 160.5 g/l cat.hr with the selectivity of 98.1% at the stage of 100 hours after starting and at the yield of 86.2 g/l cat.hr with the selectivity of 95.5% at the stage of 300 hours after starting. The reaction was stopped at the stage of 300 hours after starting and the reaction gases were purged out by flowing nitrogen at the rate of 0.1 l/hr with heating the catalyst up to 250° C. Thereafter a gaseous mixture containing steam and nitrogen (30:70 volume ratio) was introduced into the reactor for 8 hours at the rate of 100 l/hr.

Then, the catalyst was cooled down to 140° C. and the gaseous reactants were fed into the reactor again. As the results, at the stage of 100 hours after restarting, diacetoxybutene was produced at the yield of 165.3 g/l cat.hr with the selectivity of 98.3%.

These figures show the almost same values as those of the original catalyst.

EXAMPLE 26

A catalyst was prepared by means of the same method as in Example 25 and the reaction was carried out under the same conditions as in Example 25 except substituting 17.4 g of potassium fluoride for caesium chloride. At the stage of 4 hours after starting, diacetoxybutene was produced at the yield of 159.3 g/l cat.hr and at the yield of 86.6 g/l cat.hr at the stage of 200 hours after starting. At that time, the reaction was stopped and the catalyst was reactivated by introducing a gaseous mixture containing steam and nitrogen (40:60 volume ratio) at 300° C. for 10 hours. At the stage of 4 hours after restarting, it was confirmed that diacetoxybutene was produced at the yield of 152.5 g/l cat.hr.

In the following Tables, the (%) means % by molar ratio.

Table 1

| | Gram Atom Ratio of Components in Catalyst | Sampling Time after Starting (Hr) | Yield of Diacetoxybutene g/l of catalyst/Hr | Rate of Conversion to Diacetoxybutene (%) | 1,4-Diacetoxybutene-2 in Total Diacetoxybutene (%) |
|---|---|---|---|---|---|
| Example 1 | Pd : V : Sb (1 : 1 : 1) | 2 | 112.3 | 94.8 | 95.1 |
| | | 10 | 137.6 | 95.4 | 94.8 |
| | | 25 | 136.4 | 96.9 | 95.3 |
| | | 50 | 124.7 | 98.5 | 95.3 |
| Comparative Example 1 | Pd : V (1 : 1) | 2 | 16.2 | 85.0 | 82.5 |
| | | 10 | 15.3 | 84.5 | 82.8 |
| Comparative Example 2 | Pd : Sb (1 : 1) | 2 | 97.5 | 92.0 | 90.2 |
| | | 10 | 32.2 | 91.0 | 89.3 |
| | | 25 | 5.2 | — | — |

Table 2

| | Gram Atom Ratio of Components in Catalyst (Pd : V : Sb) | Sampling Time after Starting (Hr) | Yield of Diacetoxybutene (g/l of catalyst/Hr) | Rate of Conversion to Diacetoxybutene (%) | 1,4-Diacetoxybutene-2 in Total Diacetoxybutene (%) |
|---|---|---|---|---|---|
| Example 2 | 1 : 4 : 1 | 2 | 41.9 | 99.9 | 95.2 |
| | | 25 | 43.4 | 96.9 | 94.3 |
| Example 3 | 1 : 1 : 2 | 2 | 19.8 | 97.0 | 95.3 |
| | | 25 | 38.2 | 95.6 | 95.2 |
| Example 4 | 1 : 1 : 0.5 | 2 | 138.5 | 92.1 | 94.6 |
| | | 25 | 112.3 | 90.7 | 95.1 |
| Example 5 | 1 : 2 : 0.5 | 2 | 78.0 | 93.3 | 95.0 |
| | | 25 | 67.3 | 93.1 | 95.3 |
| Example 6 | 1 : 0.5 : 1 | 2 | 224.4 | 92.5 | 95.2 |
| | | 25 | 158.1 | 90.6 | 95.7 |

Table 3

| Caesium Chloride (m mol/g of carrier) | Caesium Acetate (m mol/g of carrier) | Sampling Time after Starting | Yield of Diacetoxybutene (g/l of cat.hr) | Rate of Conversion to Diacetoxybutene (%) | 1,4-Diacetoxybutene-2 in Total Diacetoxybutene (%) |
|---|---|---|---|---|---|
| | | 4 | 66.3 | 99.9 | 90.6 |

Table 3—continued

| | Caesium Chloride (m mol/g of carrier) | Caesium Acetate (m mol/g of carrier) | Sampling Time after Starting | Yield of Diacetoxybutene (g/l of cat.hr) | Rate of Conversion to Diacetoxybutene (%) | 1,4-Diacetoxy-butene-2 in Total Diacetoxybutene (%) |
|---|---|---|---|---|---|---|
| Example 9 | 1.00 | 1.00 | 50 | 110.0 | 98.2 | 93.3 |
| | | | 100 | 116.4 | 97.1 | 95.1 |
| | | | 150 | 98.8 | 96.6 | 96.5 |
| | | | 200 | 83.2 | 94.9 | 98.1 |
| Comparative Example 3 | | 1.00 | 4 | 111.7 | 96.5 | 90.1 |
| | | | 25 | 23.1 | 50.3 | 92.3 |
| | | | 50 | 0 | | |
| Comparative Example 4 | | 2.00 | 4 | 123.5 | 98.6 | 90.3 |
| | | | 25 | 25.9 | 58.5 | 94.7 |
| | | | 50 | 0 | | |
| Comparative Example 5 | 1.00 | | 4 | 0 | | |
| | | | 50 | 0 | — | — |
| | | | 100 | 0 | | |
| Comparative Example 6 | 2.00 | | 4 | 0 | | |
| | | | 50 | 0 | — | — |
| | | | 100 | 0 | | |

Table 4

| | Caesium Chloride (m mol/g of carrier) | Potassium Acetate (m mol/g of carrier) | Sampling Time after Starting | Yield of Diacetoxybutene (g/l of cat.hr) | Rate of Conversion to Diacetoxybutene (%) | 1,4-Diacetoxy-butene-2 in Total Diacetoxybutene (%) |
|---|---|---|---|---|---|---|
| | | | 4 | 55.7 | 99.9 | 88.7 |
| | | | 50 | 108.6 | 98.1 | 92.8 |
| Example 10 | 1.00 | 1.00 | 100 | 101.1 | 97.5 | 94.0 |
| | | | 150 | 81.2 | 96.1 | 95.3 |
| | | | 200 | 70.6 | 95.0 | 98.2 |
| | | | 4 | 131.0 | 98.3 | 92.2 |
| Example 11 | 1.00 | 0.50 | 50 | 147.3 | 95.5 | 92.0 |
| | | | 100 | 82.5 | 96.2 | 93.2 |
| | | | 4 | 185.5 | 97.4 | 93.7 |
| Example 12 | 0.50 | 2.00 | 50 | 116.2 | 91.8 | 92.4 |
| | | | 100 | 77.8 | 92.2 | 94.8 |

Table 5

| | Potassium Acetate (m mol/g of carrier) | Alkali Metal Halides | Alkali Metal Halides (m mol/g of carrier) | Sampling Time after Starting | Yield of Diacetoxybutene (g/l of cat.hr) | Rate of Conversion to Diacetoxybutene (%) | 1,4-Diacetoxy-butene-2 in Total Diacetoxybutene (%) |
|---|---|---|---|---|---|---|---|
| Example 13 | 1.00 | KF | 1.00 | 4 | 163.5 | 96.2 | 92.5 |
| | | | | 50 | 147.7 | 97.1 | 93.7 |
| | | | | 100 | 131.2 | 95.3 | 93.8 |
| Example 14 | 1.00 | KCl | 1.00 | 4 | 111.4 | 98.7 | 89.1 |
| | | | | 50 | 93.1 | 95.1 | 93.5 |
| | | | | 100 | 72.5 | 93.5 | 96.2 |
| Example 15 | 1.00 | NaCl | 1.00 | 4 | 82.4 | 96.2 | 91.5 |
| | | | | 50 | 73.5 | 93.5 | 93.5 |
| | | | | 100 | 66.2 | 91.6 | 96.1 |
| Example 16 | 1.00 | KBr | 1.00 | 4 | 33.5 | 100.0 | 93.1 |
| | | | | 50 | 29.3 | 100.0 | 93.6 |
| | | | | 100 | 27.2 | 100.0 | 93.7 |
| Example 17 | 1.00 | CsCl | 1.00 | 4 | 122.3 | 99.8 | 90.3 |
| | | | | 50 | 116.2 | 97.8 | 94.2 |
| | | KCl | 1.00 | 100 | 83.8 | 96.2 | 96.8 |
| Example 18 | 1.00 | CsCl | 1.00 | 4 | 75.0 | 100.0 | 91.2 |
| | | | | 50 | 71.2 | 100.0 | 94.6 |
| | | KBr | 0.10 | 100 | 66.7 | 99.8 | 94.8 |

Table 6

| | Caesium Chloride (m mol/g of carrier) | Potassium Acetate (m mol/g of carrier) | Sampling Time after Starting | Yield of Diacetoxybutene (g/l of cat.hr) | Rate of Conversion to Diacetoxybutene (%) | 1,4-Diacetoxy-butene-2 in Total Diacetoxybutene (%) | Reaction Temperature (° C) |
|---|---|---|---|---|---|---|---|
| | | | 4 | 179.9 | 99.0 | 93.6 | |
| | | | 50 | 178.3 | 98.8 | 93.8 | |
| Example 20 | 2.00 | 1.00 | 100 | 163.4 | 98.3 | 93.6 | 140 |
| | | | 200 | 127.4 | 96.9 | 94.7 | |
| | | | 400 | 71.1 | 94.7 | 97.1 | |
| | | | 100 | 195.3 | 97.7 | 95.2 | |
| Example 21 | 2.00 | 1.00 | 200 | 175.6 | 96.5 | 95.5 | 180 |
| | | | 400 | 158.9 | 94.5 | 97.7 | |
| | | | 100 | 85.0 | 100.0 | 96.7 | |
| Example 22 | 2.00 | 1.00 | 400 | 83.6 | 100.0 | 98.2 | 180 |
| | | | 700 | 82.2 | 100.0 | 98.5 | |

What is claimed is:

1. A process for producing unsaturated glycol diesters which comprises reacting in a flowing gaseous phase, a gaseous mixture comprising a conjugated diene of the formula:

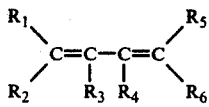

wherein, each of the $R_1$-$R_6$ groups is independently hydrogen or a hydrocarbon group of 1 to 6 carbon atoms, or wherein two of such groups are joined so that said formula includes cyclopentadiene and cyclohexadiene;
and aliphatic, alicyclic or aromatic carboxylic acid; and molecular oxygen at a temperature of 100° C. to 300° C. in the presence of a catalyst carrier, and a catalyst consisting essentially of:
   (a) palladium in the proportion of 0.1 to 10% by weight based on the weight of the carrier;
   (b) vanadium in the amount of 0.01 to 20 gram atoms per gram atom of palladium;
   (c) antimony in an amount of 0.01 to 20 grams per gram atom of palladium, the ratio of antimony to vanadium being 0.1 to 10 in terms of gram atoms, and
   (d) at least one alkali metal carboxylate in the proportion of 0.01 to 40 m mole per gram of carrier.

2. A process according to claim 1, wherein the carboxylic acid is lower aliphatic carboxylic acid.

3. A process according to claim 1, wherein said conjugated diene is presented by the following formula:

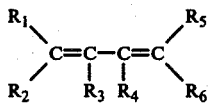

wherein $R_1$ - $R_6$ individually are hydrogen or a hydrocarbon group having 1 to 6 carbon atoms.

4. A process according to claim 1, wherein said conjugated diene is a cyclic diene.

5. A process according to claim 1, wherein said conjugated diene is butadiene, isoprene, 2,3 dimethyl butadiene, piperylene, cyclopentadiene or cyclohexadiene.

6. A process according to claim 1, wherein said carboxylic acid is acetic acid, propionic acid or butyric acid.

7. A process according to claim 1, wherein said alkali metal carboxylate is lithium-, sodium-, potassium-, rubidium- or caesium-carboxylate.

8. A process according to claim 1, wherein said vanadium is produced from ammonium metavanadate.

9. A process according to claim 1, wherein said catalyst is carried on a carrier selected from the group consisting of alumina, silica-alumina silica, active carbon, magnesia, diatomaceous earth and carborundum.

10. A process according to claim 1, wherein said catalyst contains vanadium in the ratio of 0.1 to 10 gram atoms per 1 gram atom of palladium.

11. A process according to claim 1, wherein said catalyst contains antimony in the ratio of 0.1 to 10 gram atoms per 1 gram atom of palladium.

12. A process according to claim 1, wherein said reaction is carried out at a temperature of from 100 to 200° C.

13. A process for producing unsaturated glycol diesters which comprises reacting in a flowing gaseous phase, a gaseous mixture comprising a conjugated diene of the formula:

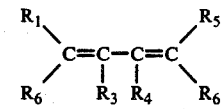

wherein, each of the $R_1$-$R_6$ groups is independently hydrogen or a hydrocarbon group of 1 to 6 carbon atoms, or wherein two of such groups are joined so that said formula includes cyclopentadiene and cyclohexadiene; and aliphatic, alicyclic or aromatic carboxylic acid; and molecular oxygen at a temperature of 100° C. to 300° C. in the presence of a catalyst carrier, and a catalyst consisting essentially of:
   (a) palladium in the proportion of 0.1 to 10% by weight based on the weight of the carrier;
   (b) vanadium in the amount of 0.01 to 20 gram atoms per gram atom of palladium;
   (c) antimony in an amount of 0.01 to 20 gram atoms per gram atom of palladium, the ratio of antimony to vanadium being 0.1 to 10 in terms of gram atoms;
   (d) at least one alkali metal carboxylate in the proportion of 0.01 to 40 m mole per gram of carrier; and
   (e) at least one alkali metal halide in an amount of 0.01 to 40 m mole per gram of carrier.

14. A process according to claim 13, wherein said alkali metal halide is lithium-, sodium-, potassium-, rubidium- or caesium-halide.

15. A process according to claim 13, wherein said conjugated diene is represented by the following formula:

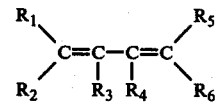

wherein $R_1$ - $R_6$ individually are hydrogen or a hydrocarbon group having 1 to 6 carbon atoms.

16. A process according to claim 13, wherein said conjugated diene is a cyclic diene.

17. A process according to claim 13, wherein said conjugated diene is butadiene, isoprene, 2,3 diemethyl butadiene, piperylene, cyclopentadiene or cyclohexadiene.

18. A process according to claim 13, wherein said carboxylic acid is a lower aliphatic carboxylic acid.

19. A process according to claim 13, wherein said carboxylic acid is acetic acid, propionic acid or butyric acid.

20. A process according to claim 13, wherein said alkali metal carboxylate is lithium-, sodium-, potassium-, rubidium- or caesium-carboxylate.

21. A process according to claim 13, wherein said vanadium is produced from ammonium metavanadate.

22. A process according to claim 13, wherein said catalyst is carried on a carrier which is alumina or silica-alumina.

23. A process according to claim 13, wherein said catalyst contains vanadium in the ratio of 0.1 to 10 gram atoms per 1 gram atom of palladium.

24. A process according to claim 13, wherein said catalyst contains antimony in the ratio of 0.1 to 10 gram atoms per 1 gram atom of palladium.

25. A process according to claim 13, wherein said reaction is carried out at a temperature of from 100 to 200° C.

* * * * *